United States Patent [19]

Lubitz

[11] Patent Number: 5,149,644
[45] Date of Patent: Sep. 22, 1992

[54] PROCESS FOR THE RELEASE OF POLY(3-HYDROXY CARBOXYLIC ACIDS)

[75] Inventor: Werner Lubitz, Munich, Fed. Rep. of Germany

[73] Assignee: PCD Polymere Gesellschaft m.b.H., Linz, Austria

[21] Appl. No.: 633,785

[22] Filed: Dec. 26, 1990

[30] Foreign Application Priority Data

Dec. 27, 1989 [AT] Austria .................................. 2942/89

[51] Int. Cl.$^5$ ................................................ C12P 7/42
[52] U.S. Cl. .................................................. 435/146
[58] Field of Search .................... 435/69.1, 146, 172.3, 435/252.33, 320.1; 536/27

[56] References Cited

U.S. PATENT DOCUMENTS

| | | | |
|---|---|---|---|
| 4,477,655 | 10/1984 | Holmes | 528/361 |
| 4,520,016 | 5/1985 | Hultmark et al. | 514/12 |

FOREIGN PATENT DOCUMENTS

| | | |
|---|---|---|
| 0046344 | 2/1982 | European Pat. Off. . |
| 0052459 | 5/1982 | European Pat. Off. . |
| 0015123 | 12/1982 | European Pat. Off. . |
| 0015699 | 5/1983 | European Pat. Off. . |
| 0145233 | 6/1985 | European Pat. Off. . |
| 0288908 | 11/1988 | European Pat. Off. . |
| 3539702 | 5/1986 | Fed. Rep. of Germany . |
| 3715840 | 12/1988 | Fed. Rep. of Germany . |
| 383754 | 1/1990 | Fed. Rep. of Germany . |

OTHER PUBLICATIONS

Slater et al., "J. Bacteriol", 170 (10) 4431–4436 (1988).
Witte et al., "Eur. J. Biochem.", 180 393–398 (1989).
Blasi et al., "J. Gen. Microbiol.", 131 1107–1114 (1985).
Chang et al., "J. Bacteriol.", 1141–1156 (Jun. 1978).

*Primary Examiner*—Richard A. Schwartz
*Assistant Examiner*—James Ketter
*Attorney, Agent, or Firm*—Wenderoth, Lind & Ponack

[57] ABSTRACT

Process for releasing poly(3-hydroxy carboxylic acid) granules from cells of Gram-negative bacteria containing the latter, by expression of a cloned natural or chimeric lysis gene, in which, before induction of lysis gene expression, the ionic strength of doubly charged cations is increased to between 0.05 and 0.5 mol/1, the expression of the lysis gene is induced by raising the temperature, the cells are harvested, and the still wet cells are resuspended in water or buffer solutions, which results in the release of the polymer granules by spontaneous lysis.

6 Claims, 1 Drawing Sheet

PROCESS FOR THE RELEASE OF POLY(3-HYDROXY CARBOXYLIC ACIDS)

The invention relates to a process for the release of homo- and/or copolymers of 3-hydroxy carboxylic acids from cells of Gram-negative bacteria containing the latter by induced lysis with the aid of a natural or chimeric lysis gene.

By homo- and/or copolymers of 3-hydroxy carboxylic acids are meant those which can be produced and stored by Gram-negative bacteria such as, for example, Alcaligenes, Athiorhodium, Pseudomonas, Rhizobium, Spirillium. In particular, these are homo- and/or copolymers of 3-hydroxybutyric acid (PHB) and of 3-hydroxyvaleric acid (PHV). However, it is also possible for these bacteria to store other poly(3-hydroxy carboxylic acids). Processes for the production and storage of PHB and PHV are described, for example, in EP-A-0,015,669, EP-A-0,046,344 and EP-A-0,052,459.

It is known from Slater et al., J. Bacteriol. 170,4431 et seq. (1988) that the enzymes responsible for producing PHB in the cell can be cloned into bacterial cells which do not produce PHB, for example into *Escherichia coli*, and can be expressed with the aid of appropriate plasmids, in which case the cloned enzymes then bring about the synthesis of PHB in the cell.

The release of poly(3-hydroxy carboxylic acids) from the cells of the microorganisms can be brought about by extraction of the polymer from the dry cells with an extractant in which the latter dissolves readily. A process of this type is described, for example, in EP-A 15,123. This necessarily entails the cells first being disrupted and thus made permeable to the relevant extractant. A disadvantage of these processes is that not only is the polymer dissolved out of the cell by the extractant but also certain cell constituents, specifically lipids, dissolve, and it is subsequently necessary to separate these impurities from the polymer.

One possibility for releasing poly(3-hydroxy carboxylic acids) from wet cells is described in EP-A-145,223. This entails the cell material being induced to dissolve enzymatically and/or by surface-active substances, with the polymer remaining undissolved. The dissolution of the cell material must in this case take place in several stages, and even then the dissolution is incomplete and undissolved cell constituents remain in the polymer.

It is also known to disrupt Gram-negative bacteria by expression of cloned lysis genes. For example, DE-A 3,715,840 describes the lysis of *E.coli* cells with the aid of a chimeric lysis gene which is controlled by a temperature-induced promoter, in which case the cells are lysed within about 30 to 70 minutes.

Witte, Lubitz, Eur. J. Biochem. 180, 393 et seq. (1989) investigated the lysis of *E. coli* with the aid of the bacteriophage lysis gene E and found that in the lysis there is formation of a small transmembrane lysis tunnel with a diameter of about 30 to 100 nm through which the cell contents are able to diffuse into the surrounding medium. The cells are lysed within about 30 to 60 minutes. Because this tunnel is very small, the use of this process for releasing polymers whose size fills almost the entire cell volume is too time-consuming on a larger scale.

SUMMARY OF THE INVENTION

It has now been possible to find a process for releasing poly(3-hydroxy carboxylic acid) granules from cells of Gram-negative bacteria containing the latter, by expression of a cloned natural or chimeric lysis gene, in which, surprisingly, there is formation not of small lysis tunnels but of orifices whose diameter comprises almost the entire cross-section of the cell, in which the cell envelopes retain their original shape, and in which the lipids anchored in the cell wall remain in the cell, it being possible for there to be complete removal of the poly(3-hydroxy carboxylic acid) granules in aqueous medium.

The invention accordingly relates to a process for releasing poly(3-hydroxy carboxylic acid) granules from cells of Gram-negative bacteria containing the latter, by expression of a cloned natural or chimeric lysis gene, which is characterised in that, before induction of lysis gene expression, the ionic strength of doubly charged cations is increased to between 0.05 and 0.5 mol/l, the expression of the lysis gene is induced by raising the temperature, the cells are harvested, and the still wet cells are resuspended in water or buffer solutions, which results in the release of the polymer granules by spontaneous lysis.

DETAILED DESCRIPTION OF THE INVENTION

Figure 1:
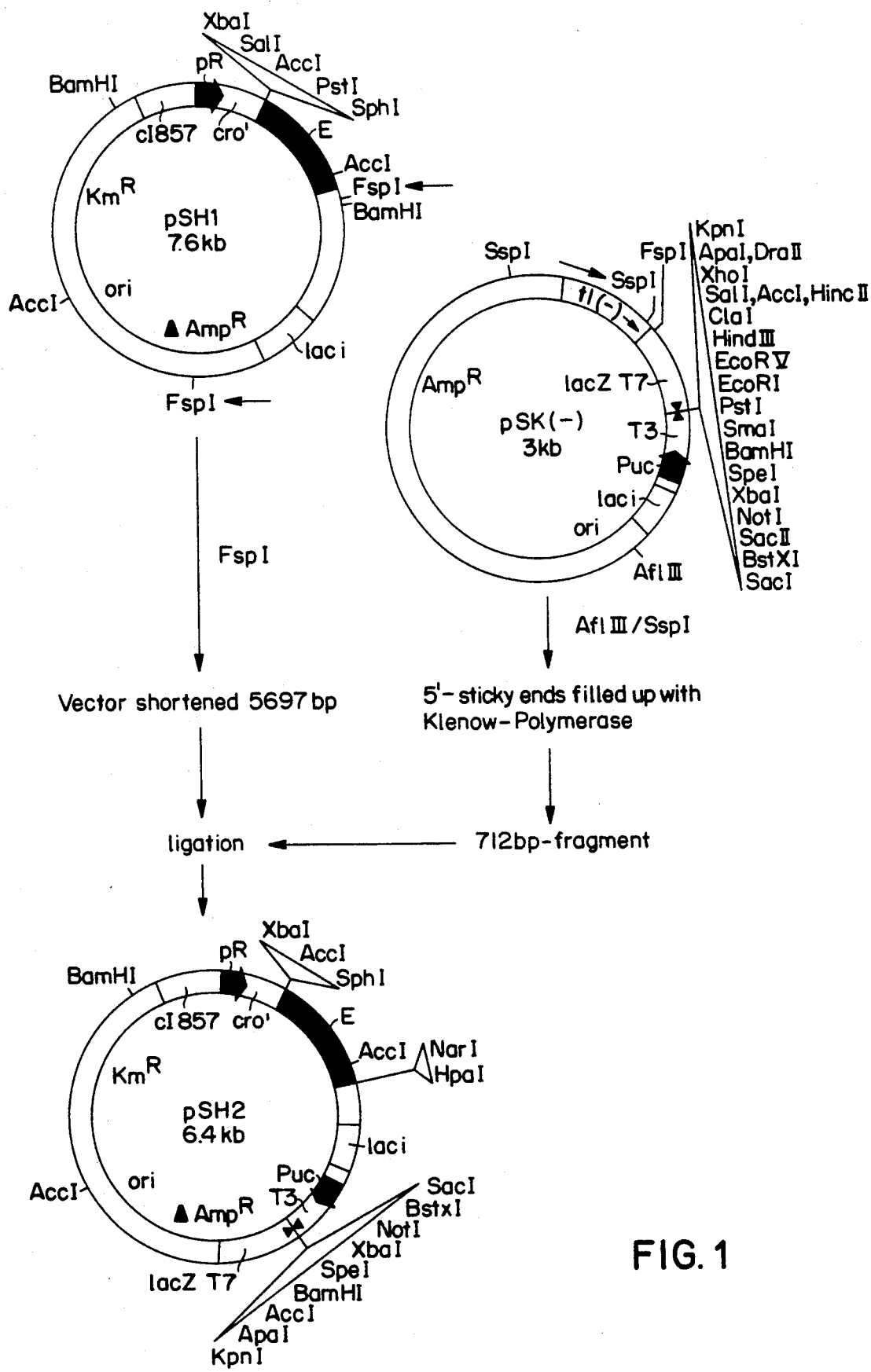
FIG. 1 shows the construction of plasmid pSH2.

To carry out the process, the Gram-negative bacteria which produce the poly(3-hydroxy carboxylic acids) are programmed for the lysis by expression of a suitable cloned lysis gene. The lysis gene can be a natural lysis gene, for example the lysis gene E of bacteriophage PhiX174, or a chimeric lysis gene. Preferably used is the cloned lysis gene E of bacteriophage PhiX174, for example on plasmid pSH2 (FIG. 1) or pAW13. To prepare plasmid pAW13, the PsH/BamHI fragment from plasmid pSB12 (Blasi et al, J. Gen. Microbiol. 131, (1985), 1107 et seq.), which contains the gene E under the control of the lambda pL promoter, is inserted into the PsH/BamHI cleavage site of pACYC177 (Chang et al. J. Bacteriol 134 (1978), 1141 et seq.). The resulting plasmid is then cut with PstI, after which it is treated with T4 DNA polymerase in order to destroy the bla gene. The plasmid pAW13 obtained in this way carries the lysis gene E under the control of the lambda pL promoter. Examples of Gram-negative bacteria which produce poly(3-hydroxy carboxylic acids) and can be programmed for the lysis are Alcaligenes, Althiorhodium, Pseudomonas. Rhizobium, Spirillium and *Escherichia coli*, into which PHB/PHV-producing enzymes are cloned.

The bacterial cells are fermented in a conventional manner, that is to say cultivated on a substrate suitable for the production of poly(3-hydroxy carboxylic acids), for example with carbohydrates as energy source, at a temperature of about 28° to 37° C. depending on the bacterium employed. It should be noted in this connection that the temperature is kept sufficiently low that the temperature-sensitive promoter of the lysis gene does not induce the lysis during the fermentation.

The concentration of doubly charged cations is then increased to about 0.05 to 0.5 mol/l, preferably to about 0.1 to 0.3 mol/l, by adding, for example, $MgSO_4$, $CaCO_3$ and the like. The lysis is now induced by raising the temperature to about 42° C., its onset is still prevented by the high ionic strength of doubly charged cations. The cells are harvested by gentle centrifugation, and the wet cell material is subsequently resuspended in water or aqueous buffer solutions, when the cells spontaneously burst, and the cytoplasmic contents and the poly(3-hydroxy carboxylic acid) granules contained therein are released within a few minutes. The water can be distilled water, deionized water or tap water. Examples of aqueous buffer solutions which can be employed are 0.001–0.01 moll TrisHCl, 0.001–0.01 mol/l $KH_2/K_2HPO_4$ buffer and the like.

The released polymer granules, the cytoplasmic contents and the empty cell envelopes can be separated by suitable methods of separation, for example by density gradient centrifugation.

EXAMPLE 1

Construction of the Cloning Vector pSH2 (FIG. 1)

The plasmid pSH1 (S. Haist, PhiX174 specific vector constructions, diploma thesis, Munich 1989) was cut with the enzyme Fsp I in the appropriate restriction buffer, resulting in a 5697 bp and a 1969 bp fragment with blunt ends. The two fragments were separated by gel electrophoresis and purified using "Gene Clean" (supplied by Bio 101 Inc.).

The plasmid pBluescript pSK(−) (supplied by Stratagene) was cut with the restriction enzymes SspI, which forms blunt ends, and Afl III, which forms 5′-protruding ends, in the appropriate restriction buffer, resulting in three fragments of 1697 bp, 712 bp and 555 bp. The 712 bp fragment was eluted with "Gene Clean", and the 5′-protruding end was filled in with Klenow polymerase. The 5697 bp fragment from pSH1 was ligated with this 712 bp fragment with the aid of T4 DNA ligase in the appropriate buffer.

EXAMPLE 2

Transformation of E. coli PC 1363 (Phabagen Collection, Utrecht University)

The transformation of E. coli PC 1363 is carried out in a manner known per se, for example by the method described in Maniatis et al. Molecular Cloning, Cold Spring Harbor Laboratory, New York (1982).

For this purpose, 5 ml of Lurea Broth, a nutrient medium consisting of 10 g of peptone, 5 g of yeast extract, 5 g of NaCl in 1000 ml of distilled water (pH 7), are inoculated with 1 ml of preculture of E. coli PC 1363 and shaken at 37° C. The cells are harvested by centrifugation and suspended in 25 ml of transformation buffer consisting of 150 mmol/l KCl, 50 mmol/l $MgCl_2$ and 1 mmol/l TrisHCl in ice. After renewed centrifugation, the cells are resuspended in 2 ml of transformation buffer. 0.1 ml of this suspension is mixed with plasmid DNA (pSH2 (p15A) and pSB20-PHB (pHB1 (Slater et al. J. Bacteriol. 170, p 4431 et seq. (1988)))and, after about 1 hour, 1.2 ml of Lurea broth are added at 28° C.

The transformants were selected in accordance with the antibiotic resistance markers of the plasmids.

EXAMPLE 3

FERMENTATION AND LYSIS OF E. COLI PC 1363 (pSB20, pSH2)

10 ml of Lurea Broth were inoculated with an overnight culture of the E. coli strain prepared as in Example 2 and cultivated at 28° C. until the optical density $OD_{600}$ was 0.2–0.9. Then a 2 mol/l $MgSO_4$ solution was added until the final concentration was 0.2 mol/l, and the mixture was incubated at 28° C. for 30 min. The temperature was then raised to 42° C. and, after 30 min, the cells were harvested by centrifugation (7000 rpm, 5 min) at 4° C., and the cell material was resuspended in 10 ml of distilled water. Lysis takes place during the suspension within 10 min.

Sucrose was added to the lysed cell mixture to a final concentration of 55%, and it was then covered with layers of 50, 45 and 40% strength sucrose solution in 3 mmol/l EDTA. After centrifugation (4° C., 37,000 rpm, SW41Ti) for 16 hours, the gradient was fractionated, and the protein content, the density and the content of PHB/PHV was determined. Three fractions with densities of 1.24 g/ml (unlysed cells), 1.22 g/ml (cell ghosts) and 1.20 g/ml (PHB/PHV) were obtained. 60 to 80% of PHB/PHV granules were released by this.

What I claim is:

1. Process for releasing poly(3-hydroxy carboxylic acid) granules from cells of Gram-negative bacteria containing the latter and divalent cations, by expression of a cloned natural or chimeric lysis gene, wherein, before induction of lysis gene expression, the ionic concentration of divalent cations is increased to between 0.05 and 0.05 mol/l, the expression of the lysis gene is induced by raising the temperature, the cells are harvested by gentle centrifugation, and the still wet cells are resuspended in water or buffer solutions, which results in the release of the polymer granules by spontaneous lysis.

2. Process according to claim 1, wherein the lysis gene employed is the cloned lysis gene E of bacteriophage PhiX174.

3. Process according to claim 1, wherein the concentration of the divalent cations is raised to between 0.1 and 0.3 mol/l.

4. Process according to claim 1, wherein the concentration of the divalent cations is raised by adding $MgSO_4$ or $CaCO_3$.

5. Process according to claim 1, wherein Alcaligenes are employed as Gram-negative bacteria.

6. Process according to claim 1, wherein transformed E. coli are employed as Gram-negative bacteria.

* * * * *